US00PP10259P

United States Patent [19]

Cosner et al.

[11] Patent Number: Plant 10,259

[45] Date of Patent: Feb. 24, 1998

[54] GUINEA IMPATIENS PLANT NAMED 'ELECTRA HOT WHITE'

[76] Inventors: Harlan B. Cosner; Sue L. Cosner, both of P.O. Box 173, Broadbent, Oreg. 97414

[21] Appl. No.: 772,503

[22] Filed: Dec. 23, 1996

[51] Int. Cl.[6] ..... A01H 5/00

[52] U.S. Cl. ..... Plt./87.6

[58] Field of Search ..... Plt./87.6

*Primary Examiner*—James R. Feyrer

*Attorney, Agent, or Firm*—C. A. Whealy

[57] ABSTRACT

A new and distinct cultivar of New Guinea Impatiens plant named 'Electra Hot White', characterized by its large pure white flowers; flowers held above the foliage; rounded flower form; numerous flowers per plant; freely branching, dense and bushy plant habit; moderately vigorous and compact, rounded plant habit; dark green and glossy foliage that is flat and horizontal to the plant.

1 Drawing Sheet

The present invention relates to a new and distinct cultivar of New Guinea Impatiens plant, botanically known as *Impatiens hawkeri*, and hereinafter referred to by the cultivar name 'Electra Hot White'.

The new cultivar is a product of a planned breeding program conducted by the inventors in Coquille, Oreg. The objective of the breeding program was to develop varieties with uniform plant habit, attractive flower colors, good flower form, and numerous flowers per plant.

The new cultivar originated from a cross made in November, 1993, by the inventors of two unnamed proprietary seedling selections.

The cultivar 'Electra Hot White' was discovered and selected by the inventors as a flowering plant within the progeny of the stated cross in a controlled environment in Coquille, Oreg. Asexual reproduction of the new cultivar by terminal cuttings taken at Coquille, Oreg., has shown that the unique features of this new New Guinea Impatiens are stable and reproduced true to type in successive generations of asexual reproduction.

The following traits have been repeatedly observed and are determined to be unique characteristics of 'Electra Hot White'. These characteristics in combination distinguish the new New Guinea Impatiens as a new and distinct cultivar:

1. Large pure white flowers.
2. Flowers held above the foliage.
3. Rounded flower form.
4. Numerous flowers per plant.
5. Freely branching, dense and bushy plant habit.
6. Moderately vigorous and compact, rounded plant habit.
7. Dark green and glossy foliage that is flat and horizontal.

In contrast to plants of the new New Guinea Impatiens, plants of the parent proprietary seedling selections have lighter green foliage, more upright habit, and smaller flowers.

The new New Guinea Impatiens is similar in flower color to the New Guinea Impatiens cultivar BSR-203 Pure White (disclosed in U.S. Plant Pat. No. 8,410). However, in side-by-side comparisons in Coquille, Oreg., under commercial practice, plants of the new New Guinea Impatiens differed from plants of the cultivar BSR-203 Pure White in the following characteristics:

1. Leaves of plants of the new New Guinea Impatiens are darker green than leaves of plants of the cultivar BSR-203 Pure White.

2. Stems of plants of the new New Guinea Impatiens are green whereas stems of plants of the cultivar BSR-203 Pure White have a brownish tinge.

3. Plants of the new New Guinea Impatiens flower earlier than flowers of plants of the cultivar BSR-203 Pure White.

4. Flowers of plants of the new New Guinea Impatiens are displayed higher above the foliage than flowers of plants of the cultivar BSR-203 Pure White.

5. Flowers of plants of the new New Guinea Impatiens are larger and more rounded than flowers of plants of the cultivar BSR-203 Pure White.

The new New Guinea Impatiens is also similar in flower color to the New Guinea Impatiens cultivar Moorea (disclosed in U.S. Plant Pat. No. 9,147). However in side-by-side comparisons in Coquille, Oreg., under commercial practice, plants of the new New Guinea Impatiens differed from plants of the cultivar Moorea in the following characteristics:

1. Plants of the new New Guinea Impatiens are rounded in plant shape whereas plants of the cultivar Moorea are more upright.

2. Leaves of plants of the new New Guinea Impatiens are horizontal to the plant whereas leaves of plants of the cultivar Moorea are orientated upwards.

3. Leaves of plants of the new New Guinea Impatiens are longer than leaves of plants of the cultivar Moorea.

4. Plants of the new New Guinea Impatiens flower about one week earlier than flowers of plants of the cultivar Moorea.

5. Plants of the new New Guinea Impatiens have more flowers per lateral stem than of plants of the cultivar Moorea.

6. Flowers of plants of the new New Guinea Impatiens are displayed above the foliage whereas flowers of plants of the cultiar Moorea are often down in the foliage due to the longer peduncles on plants of the new New Guinea Impatiens.

7. Flowers of plants of the new New Guinea Impatiens are flat whereas flowers of plants of the cultiar Moorea are slightly cupped.

A detailed comparison of plants of the new New Guinea Impatiens and the cultivar Moorea appears in Chart A at the end of the specification.

The new New Guinea Impatiens has not been observed under all possible environmental conditions. The phenotype may vary significantly with variations in environment such as temperature and light level, without, however, any variance in genotype.

The accompanying colored photographs illustrate the overall appearance and flower color of the new New Guinea Impatiens, showing the colors as true as it is reasonably possible to obtain in colored reproductions of this type.

The first photograph comprises a side perspective view of a typical plant of the new New Guinea Impatiens.

The second photograph comprises a side perspective view of typical plants of the cultivar Moorea (left) and the new New Guinea Impatiens (right) showing the differences in plant and flowering habit. Flower and foliage colors in the photographs may appear different from the actual colors due to light reflectance.

The following observations, measurements, values, and comparisons describe plants grown in Coquille, Oreg., grown under double layer of polyethylene with day temperatures ranging from 23 to 30C and night temperatures ranging from 10 to 18C, and light levels ranging from 3,000 to 5,000 footcandles.

In the following description, color references are made to The Royal Horticultural Society Colour Chart except where general terms of ordinary dictionary significance are used.

Botanical classification: *Impatiens hawkeri* cultivar 'Electra Hot White'.

Parentage:

*Male or pollen parent.*—Unnamed proprietary seedling selection.

*Female or seed parent.*—Unnamed proprietary seedling selection.

Propagation:

*Type cutting.*—Terminal cuttings.

*Time to initiate roots.*—About 24 days at a temperature of 20C.

*Rooting habit.*—Numerous, fibrous, and well-branched.

Plant description:

*Form.*—Rounded plant form.

*Growth habit.*—Moderately vigorous and compact. Freely branching, dense and bushy growth. Flowers above or beyond the foliage. Suitable for 10 to 25-cm containers. Leaves horizontal to plant.

*Plant height.*—About 15 cm.

*Lateral branches.*—Size: Length: About 11 cm. Diameter: About 8 mm. Color: 144A.

*Foliage description.*—Leaves simple, generally symmetrical, abundant, opposite or in whorls of three, horizontal to plant and flat in aspect. Size, largest leaves: Length: About 9.5 cm. Width: About 3.25 cm. Shape: Ovate with acuminate apex, attenuate base and ciliate margin. Texture: Smooth, glossy. Color: Upper surface: 147A. Lower surface: 147B. Venation, upper surface: 147B. Venation lower surface: 147B. Petiole: Size: Length: About 2.25 cm. Diameter: About 3 mm. Color: 147C.

Flower description:

*Flower type and habit.*—Large pure white flowers. Freely and continuously flowering. Flowers arise from leaf axils. Usually eight flowers per lateral branch. Flowers positioned above or beyond the foliage and face upward or outward. Flowers flat and rounded. Flowers self-cleaning.

*Time to flower.*—Flowering generally commences four to six weeks after planting.

*Flowering season.*—Year-round under greenhouse conditions. In the garden, flowering is continuous from spring until fall.

*Flower size.*—Length: About 6 cm. Width: About 6.5 cm. Depth: About 5 mm.

*Flower buds.*—Size: Length: About 1.7 cm. Diameter: About 1.2 cm. Shape: Ovoid. Rate of opening: 2 to 3 days. Color: White.

*Petals.*—Quantity: Five. Size (largest petals): Length: Top petal: About 2.5 cm. Middle petals: About 3 cm. Bottom petals: About 3.5 cm. Width: Top petal: About 3.5 cm. Middle petals: About 2.5 cm. Bottom petals: About 3 cm. Shape: Cordate with emarginate apex, cuneate or obtuse base and entire margin. Texture: Satiny, smooth. Color: When opening, upper surface: Iridescent, 155D. When opening, lower surface: Iridescent, 155D. Mature, upper surface: Iridescent, 155D. Mature, lower surface: Iridescent, 155D. Fading to: Iridescent, 155D.

*Spur.*—Length: About 4.5 cm. Shape: Narrow and curved. Color: 145A.

*Peduncles.*—Length: About 5 cm. Angle: Upright. Strength: Strong. Color: 145A.

*Reproductive organs.*—Androecium: Anther shape: Lobate. Anther size: 6 by 4 mm. Anther color: White. Amount of pollen: Moderate. Gynoecium: Stigma color: White. Style length: About 4 mm. Style color: Green. Ovary color: Green.

Disease resistance: Under commercial conditions, resistance nor susceptibility to pathogens has not been observed.

CHART A

| CHARACTERISTIC | 'ELEVTRA HOT WHITE' | 'MOOREA' |
|---|---|---|
| GROWTH HABIT | Rounded, leaves horizontal | Upright, leaves orientated upwards |
| PLANT HEIGHT | About 15 cm | About 16 cm |
| LATERAL BRANCH LENGTH | About 11 cm | About 12 cm |
| LATERAL BRANCH DIAMETER | About 8 mm | About 7 mm |
| LEAF LENGTH | About 9.5 cm | About 9 cm |
| LEAF WIDTH | About 3.25 cm | About 3.25 cm |
| PETIOLE LENGTH | About 2.25 cm | About 1.5 cm |
| PETIOLE DIAMETER | About 3 mm | About 2.5 mm |
| FLOWER POSITION/ ASPECT | Flowers above the foliage, flowers flat | Flowers down in the foliage, flowers slightly cupped |
| TIME TO FLOWER | One week before Moorea | One week after Electra Hot White |
| QUANTITY OF FLOWERS AND BUDS PER LATERAL STEM | About 8 | About 6 |
| SPUR COLOR | 145A | 145C |
| PEDUNCLE LENGTH | About 5 cm | About 4 cm |

It is claimed:

1. A new and distinct New Guinea Impatiens plant named 'Electra Hot White', as illustrated and described.

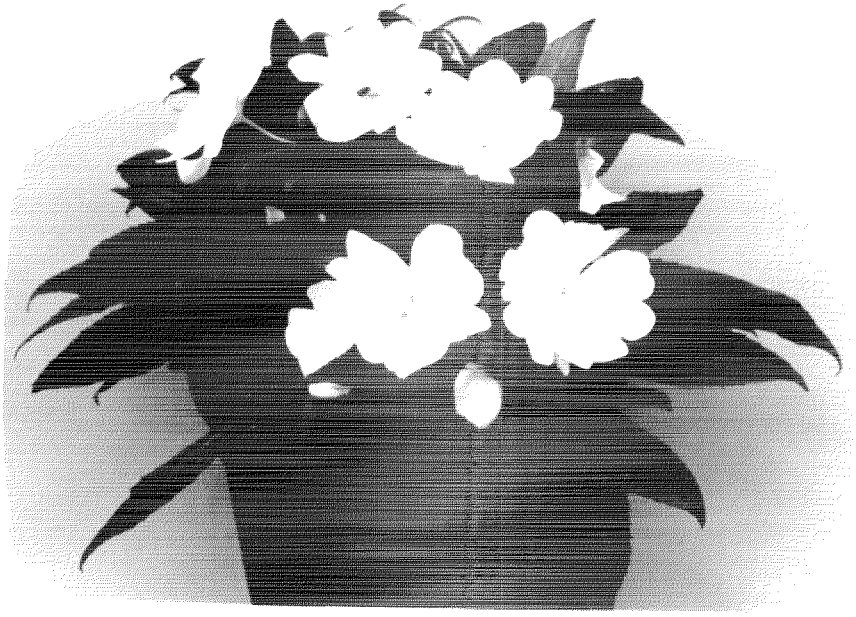
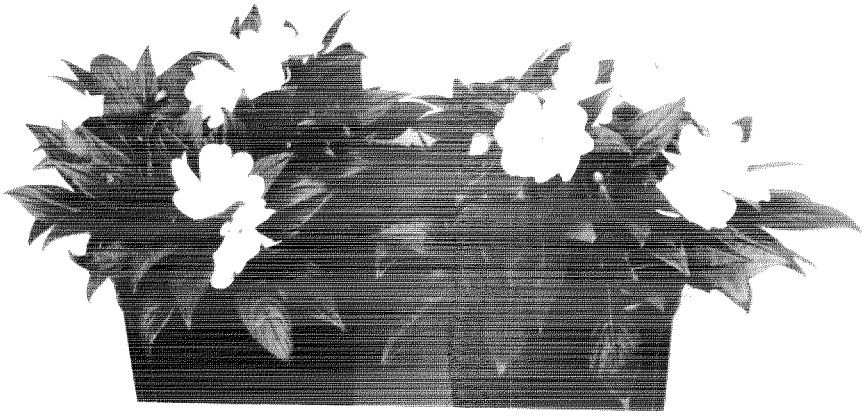

* * * * *